United States Patent
Tseng

(10) Patent No.: US 12,209,955 B1
(45) Date of Patent: Jan. 28, 2025

(54) DEVICE AND METHOD FOR GAS CONCENTRATION MEASUREMENT

(71) Applicant: Finesse Technology Co., Ltd., Hsinchu County (TW)

(72) Inventor: Shin-Hua Tseng, Hsinchu County (TW)

(73) Assignee: Finesse Technology Co., Ltd., Hsinchu (TW)

( * ) Notice: Subject to any disclaimer, the term of this patent is extended or adjusted under 35 U.S.C. 154(b) by 0 days.

(21) Appl. No.: 18/671,912

(22) Filed: May 22, 2024

(30) Foreign Application Priority Data

Sep. 19, 2023 (TW) .................. 112135671

(51) Int. Cl.
*G01N 21/33* (2006.01)
*G01N 33/00* (2006.01)

(52) U.S. Cl.
CPC ......... *G01N 21/33* (2013.01); *G01N 33/0027* (2013.01); *G01N 2201/127* (2013.01)

(58) Field of Classification Search
CPC .................................................. G01N 21/33
See application file for complete search history.

(56) References Cited

U.S. PATENT DOCUMENTS

2021/0109014 A1* 4/2021 Heffels .................. G01N 21/61

FOREIGN PATENT DOCUMENTS

| CN | 1844893 A | 10/2006 |
|---|---|---|
| CN | 106501192 A | 3/2017 |
| CN | 106872366 A | 6/2017 |
| JP | 2010210594 A | 9/2010 |
| JP | 2011149965 A | 8/2011 |
| JP | 2016050793 A | 4/2016 |
| JP | 2024076641 A | 6/2024 |
| TW | 202332898 A | 8/2023 |

OTHER PUBLICATIONS

Suitable for measurement and analysis of green and environmentally friendly industries such as semiconductors, agriculture and water resources.

* cited by examiner

*Primary Examiner* — Dani Fox
*Assistant Examiner* — Casey Bryant

(57) ABSTRACT

Disclosed are a device and a method for gas concentration measurement comprising a gas detection chamber, a temperature sensing element, a pressure sensing element, a light source supply device and a light sensing device for measuring a gas concentration of a to-be-measured gas (such as ozone). The temperature sensing element and the pressure sensing element respectively measure a temperature and a pressure of the to-be-measured gas. The light source supply device uses UV-LED as an ultraviolet light-emitting source, and provides a first detection light beam and a calibration light beam with different ozone absorbances, and then uses a light beam splitter to split the light beams into a split light that passes through the to-be-measured gas and a split light that does not pass through the to-be-measured gas.

22 Claims, 5 Drawing Sheets

DEVICE AND METHOD FOR GAS CONCENTRATION MEASUREMENT

CROSS-REFERENCE TO RELATED APPLICATION

This application claims priority from Taiwan Patent Application No. 112135671, filed on Sep. 19, 2023, each of which is hereby incorporated herein by reference in its entireties.

BACKGROUND OF THE DISCLOSURE

1. Field of Disclosure

The disclosure relates to a device and a method for measuring, more particularly to a device and a method for gas concentration measurement.

2. Related Art

With the gradual development of industries, various gases are often used in various industries or living environments. For example, ozone is often used in sterilization equipment and semiconductor wafer manufacturing. However, the instruments used to measure ozone concentration on the market can no longer meet the requirements for accurate, stable and rapid feedback of ozone concentration. The current ozone concentration measurement instruments use the ultraviolet absorbance method, the ultraviolet light-emitting source emits ultraviolet light to penetrate the ozone in the quartz glass tube, and use a light sensor to measure the light sensing signal, and then calculate the concentration of the ozone by using the Beer-Lambert Equation.

However, existing ozone concentration measurement instruments mainly use low-pressure mercury lamps as ultraviolet light-emitting sources. Although low-pressure mercury lamps can provide ultraviolet light-emitting sources close to the ozone absorption spectrum, low-pressure mercury lamp technology has the following long-standing drawbacks that are difficult to solve: (1) It requires a long warm-up time, which requires a period of time before measurement can be performed again. (2) A high-voltage power supply is required, resulting in large energy consumption in measurement. (3) The ultraviolet light-emitting source radiates to all directions, resulting in low utilization rate. (4) Due to its large size, one set of device can only have one light-emitting source with a fixed wavelength. When there are huge differences in the ozone concentration range, different devices need to be replaced. (5) Shorter service life. (6) Mercury vapor will be generated.

In addition, when the wall of the quartz glass tube is contaminated or deposited during the ozone measurement process, it may cause an error in the light sensing signal measured by the light sensor. However, existing ozone concentration measurement instruments cannot provide instant feedback and instant calibration for this error. It can be known from this that existing ozone concentration measuring instruments obviously do not meet the requirements for accurate, stable and rapid feedback of ozone concentration.

SUMMARY OF THE DISCLOSURE

In order to solve the problems that a warm-up time is too long, a starting voltage is too high, a light-emitting source utilization rate is too low, and small detecting concentration range caused by using a single wavelength in the traditional technology that uses low-pressure mercury lamps as ultraviolet light-emitting sources when measuring a concentration of ozone gas, one object of the disclosure is to provide a device for gas concentration measurement for measuring a gas concentration of a to-be-measured gas.

In order to achieve the aforementioned object, the disclosure discloses a device for gas concentration measurement for measuring a gas concentration of a to-be-measured gas, at least comprising: a gas detection chamber, the gas detection chamber is communicated to a gas inlet and outlet channel, so that a cavity of the gas detection chamber contains the to-be-measured gas; a temperature sensing element for detecting a gas temperature of the to-be-measured gas in the cavity of the gas detection chamber; a pressure sensing element for detecting a gas pressure of the to-be-measured gas in the cavity of the gas detection chamber; a light source supply device provided on a first side of the gas detection chamber, comprising: at least one light-emitting source for providing a first detection light beam and a calibration light beam, wherein an absorbance of the to-be-measured gas for the first detection light beam is greater than an absorbance of the to-be-measured gas for the calibration light beam; and a light beam splitter for splitting the first detection light beam into a first detection split light and a second detection split light and splitting the calibration light beam into a first calibration split light and a second calibration split light, wherein the first detection split light and the first calibration split light pass through the gas detection chamber and the to-be-measured gas in the gas detection chamber, the second detection split light and the second calibration split light do not pass through the gas detection chamber and the to-be-measured gas in the gas detection chamber; and a light sensing device, the light sensing device at least comprises a first light sensing element and a second light sensing element respectively located on a second side and the first side of the gas detection chamber for respectively measuring a light intensity of the first detection split light and a light intensity of the second detection split light of the first detection light beam, thereby calculating a first detection concentration of the to-be-measured gas, and measuring a light intensity of the first calibration split light and a light intensity of the second calibration split light of the calibration light beam respectively, thereby calculating a calibration concentration of the to-be-measured gas, wherein the gas concentration of the to-be-measured gas is obtained after subtracting the calibration concentration from the first detection concentration, wherein when the gas concentration of the to-be-measured gas obtained after subtracting the calibration concentration from the first detection concentration is lower than a preset value, the light-emitting source provides at least one second detection light beam to replace the first detection light beam, and a wavelength and/or a brightness of the second detection light beam are/is different from a wavelength and/or a brightness of the first detection light beam.

Preferably, two ends of the gas inlet and outlet channel are respectively a channel air inlet hole and a channel air outlet hole for correspondingly introducing and exporting the to-be-measured gas, and the gas detection chamber is a hollow chamber having the cavity, two ends of the hollow chamber having a detection gas inlet hole and a detection gas outlet hole respectively communicated to the cavity of the hollow chamber, wherein the to-be-measured gas continuously flows through the cavity of the hollow chamber of the gas detection chamber.

Preferably, the device for gas concentration measurement further comprises a processing element calculating the first detection concentration of the to-be-measured gas based on the gas temperature of the to-be-measured gas, the gas pressure of the to-be-measured gas, the light intensity of the first detection split light, the light intensity of the second detection split light, an optical path length of the to-be-measured gas in the cavity of the gas detection chamber, and an absorption coefficient of the to-be-measured gas, wherein the processing element further calculates the calibration concentration of the to-be-measured gas based on the gas temperature of the to-be-measured gas, the gas pressure of the to-be-measured gas, the light intensity of the first calibration split light, the light intensity of the second calibration split light, the optical path length of the to-be-measured gas in the cavity of the gas detection chamber, and the absorption coefficient of the to-be-measured gas.

Preferably, the to-be-measured gas is ozone, and the first detection light beam and the calibration light beam provided by the light-emitting source are ultraviolet light.

Preferably, the light beam splitter is a tilted light beam splitting plate to cause the first detection split light and the first calibration split light having a same first optical path, the second detection split light and the second calibration split light having a same second optical path. Preferably, the gas detection chamber is a quartz glass tube.

Preferably, the wavelength of the first detection light beam is within an absorption wavelength range of the to-be-measured gas, and a wavelength of the calibration light beam is outside the absorption wavelength range of the to-be-measured gas, thereby calibrating a light absorbance interference error generated by the gas detection chamber.

Preferably, the light source supply device further comprises a light source control element for controlling the light-emitting source of the light source supply device to alternately provide the first detection light beam and the calibration light beam in a light-emitting mode.

Preferably, the light-emitting mode is pulse type or interval type opening and closing to provide the first detection light beam and the calibration light beam.

Preferably, when the gas concentration of the to-be-measured gas obtained after subtracting the calibration concentration from the first detection concentration is lower than 10% of a preset scale, the light-emitting source provides the at least one second detection light beam to replace the first detection light beam, and the wavelength and/or the brightness of the second detection light beam are/is different from the wavelength and/or the brightness of the first detection light beam.

Preferably, the light-emitting source has one light-emitting element or a plurality of light-emitting elements for providing the first detection light beam and the calibration light beam.

In order to achieve the aforementioned object, the disclosure discloses a method for gas concentration measurement for measuring a gas concentration of a to-be-measured gas, at least comprising following steps of: providing a gas detection chamber, the gas detection chamber communicating to a gas inlet and outlet channel, so that a cavity of the gas detection chamber contains the to-be-measured gas; performing a temperature detection step for detecting a gas temperature of the to-be-measured gas; performing a pressure detection step for detecting a gas pressure of the to-be-measured gas; providing a first detection light beam and a calibration light beam, wherein an absorbance of the to-be-measured gas for the first detection light beam is greater than an absorbance of the to-be-measured gas for the calibration light beam; performing a spectroscopic step for splitting the first detection light beam into a first detection split light and a second detection split light respectively passing through and not passing through the gas detection chamber and the to-be-measured gas in the gas detection chamber, and splitting the calibration light beam into a first calibration split light and a second calibration split light respectively passing through and not passing through the gas detection chamber and the to-be-measured gas in the gas detection chamber; performing a light intensity measurement step for measuring a light intensity of the first detection split light and a light intensity of the second detection split light of the first detection light beam, thereby calculating a first detection concentration of the to-be-measured gas; and performing a calibration step for measuring a light intensity of the first calibration split light and a light intensity of the second calibration split light of the calibration light beam respectively, thereby calculating a calibration concentration of the to-be-measured gas, wherein the gas concentration of the to-be-measured gas is obtained after subtracting the calibration concentration from the first detection concentration, wherein when the gas concentration of the to-be-measured gas obtained after subtracting the calibration concentration from the first detection concentration is lower than a preset value, providing at least one second detection light beam to replace the first detection light beam, and a wavelength and/or a brightness of the second detection light beam are/is different from a wavelength and/or a brightness of the first detection light beam.

Preferably, the to-be-measured gas continuously flows through the cavity of the gas detection chamber.

Preferably, the light intensity measurement step further comprises calculating the first detection concentration of the to-be-measured gas based on the gas temperature of the to-be-measured gas, the gas pressure of the to-be-measured gas, the light intensity of the first detection split light, the light intensity of the second detection split light, an optical path length of the to-be-measured gas in the cavity of the gas detection chamber, and an absorption coefficient of the to-be-measured gas, and the calibration step further comprises calculating the calibration concentration of the to-be-measured gas based on the gas temperature of the to-be-measured gas, the gas pressure of the to-be-measured gas, the light intensity of the first calibration split light, the light intensity of the second calibration split light, the optical path length of the to-be-measured gas in the cavity of the gas detection chamber, and the absorption coefficient of the to-be-measured gas.

Preferably, the to-be-measured gas is ozone, and the first detection light beam and the calibration light beam are ultraviolet light.

Preferably, the spectroscopic step uses a light beam splitter to cause the first detection split light and the first calibration split light having a same first optical path, the second detection split light and the second calibration split light having a same second optical path.

Preferably, the gas detection chamber is a quartz glass tube.

Preferably, the wavelength of the first detection light beam is within an absorption wavelength range of the to-be-measured gas, and a wavelength of the calibration light beam is outside the absorption wavelength range of the to-be-measured gas, thereby calibrating a light absorbance interference error generated by a material of the gas detection chamber.

Preferably, the method for gas concentration measurement further comprises using a light source control element for controlling a light-emitting source to alternately provide the first detection light beam and the calibration light beam in a light-emitting mode.

Preferably, the light-emitting mode is pulse type or interval type opening and closing to provide the first detection light beam and the calibration light beam.

Preferably, when the gas concentration of the to-be-measured gas obtained after subtracting the calibration concentration from the first detection concentration is lower than 10% of a preset scale, providing the at least one second detection light beam to replace the first detection light beam, and the wavelength and/or the brightness of the second detection light beam are/is different from the wavelength and/or the brightness of the first detection light beam.

Preferably, the method for gas concentration measurement further comprises using a light-emitting source having one light-emitting element or a plurality of light-emitting elements for providing the first detection light beam and the calibration light beam.

Based on the above, the device and the method for gas concentration measurement of the disclosure have the following efficacies:

(1) Compared with the traditional technology of using a low-pressure mercury lamp as an ultraviolet light-emitting source, the device for gas concentration measurement of the disclosure uses a small light-emitting diode element as an ultraviolet light-emitting source (UV-LED), which could respond to ozone gas in different concentration ranges, so there is no need to replace the machine.

(2) The disclosure uses the light-emitting diode element as the ultraviolet light-emitting source and does not require startup warm-up time. Therefore, the ultraviolet light-emitting source could be provided in a pulse switch manner to achieve instant calibration.

(3) The disclosure uses the light-emitting diode element as the ultraviolet light-emitting source to instantly, accurately and quickly measure a gas concentration of the continuously flowing to-be-measured gas. It does not require preheating, has low starting voltage, does not have mercury vapor, and has a long service life.

(4) The disclosure could instantly change and provide detection light beams of different wavelengths in response to the to-be-measured gas in different concentration ranges, thereby providing real-time calibration and feedback.

(5) The disclosure could solve the problem of measurement errors caused by contaminated quartz glass tube walls in the traditional technology.

In order to enable the examiner to have a further understanding and recognition of the technical features of the disclosure, preferred embodiments in conjunction with detailed explanation are provided as follows.

DETAILED DESCRIPTION OF THE DISCLOSURE

Figure 1:
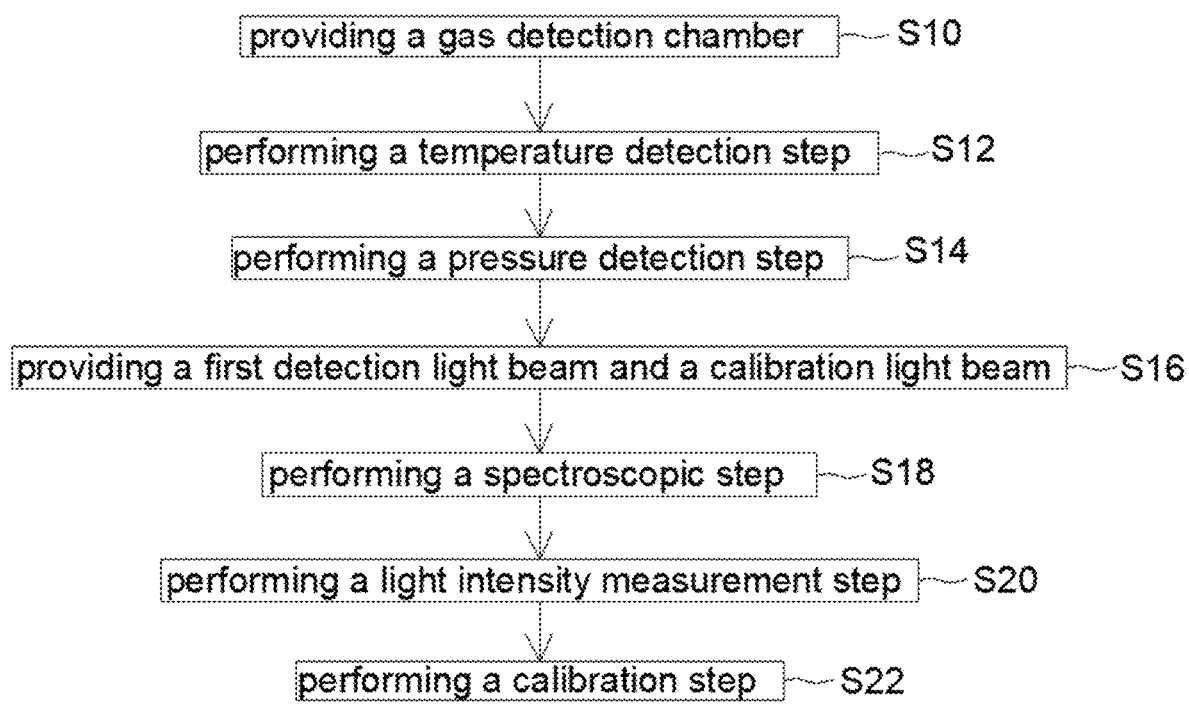
FIG. 1 is a flow chart of a method for gas concentration measurement of the disclosure.

In order to understand the technical features, content and advantages of the disclosure and its achievable efficacies, the disclosure is described below in detail in conjunction with the figures, and in the form of embodiments, the figures used herein are only for a purpose of schematically supplementing the specification, and may not be true proportions and precise configurations after implementation of the disclosure; and therefore, relationship between the proportions and configurations of the attached figures should not be interpreted to limit the scope of the claims of the disclosure in actual implementation. In addition, in order to facilitate understanding, the same elements in the following embodiments are indicated by the same referenced numbers. And the size and proportions of the components shown in the drawings are for the purpose of explaining the components and their structures only and are not intending to be limiting.

Unless otherwise noted, all terms used in the whole descriptions and claims shall have their common meaning in the related field in the descriptions disclosed herein and in other special descriptions. Some terms used to describe in the present disclosure will be defined below or in other parts of the descriptions as an extra guidance for those skilled in the art to understand the descriptions of the present disclosure.

The terms such as "first", "second", "third", "fourth" used in the descriptions are not indicating an order or sequence, and are not intending to limit the scope of the present disclosure. They are used only for differentiation of components or operations described by the same terms.

Moreover, the terms "comprising", "including", "having", and "with" used in the descriptions are all open terms and have the meaning of "comprising but not limited to".

In order to solve the problems that a warm-up time is too long, a starting voltage is too high, a light-emitting source utilization rate is too low, and small detecting concentration range caused by using a single wavelength in the traditional technology that uses low-pressure mercury lamps as ultraviolet light-emitting sources when measuring a concentration of ozone gas, the disclosure discloses a device and a method for gas concentration measurement for measuring a gas concentration of a to-be-measured gas (such as continuously flowing ozone). A light-emitting source of a light source supply device of the disclosure provides at least more than one (inclusive) ultraviolet light wavelength to accurately and quickly measure ozone concentration. The disclosure could solve the problems of using a low-pressure mercury lamp as an ultraviolet light-emitting source in the traditional technology, and solve the problem of measurement errors caused by contaminated quartz glass tube walls in the traditional technology.

Figure 2:
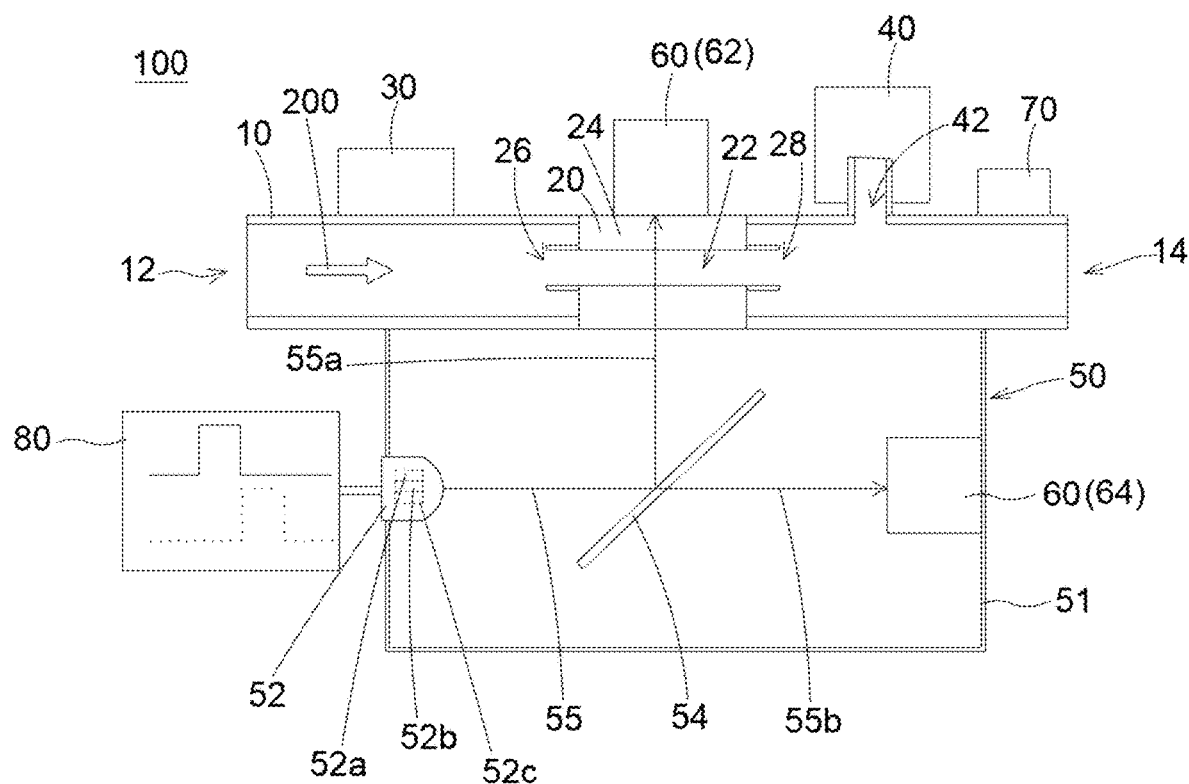
FIG. 2 is a schematic diagram of a device for gas concentration measurement of the disclosure, in which a light-emitting source generates a first detection light beam.
Figure 3:
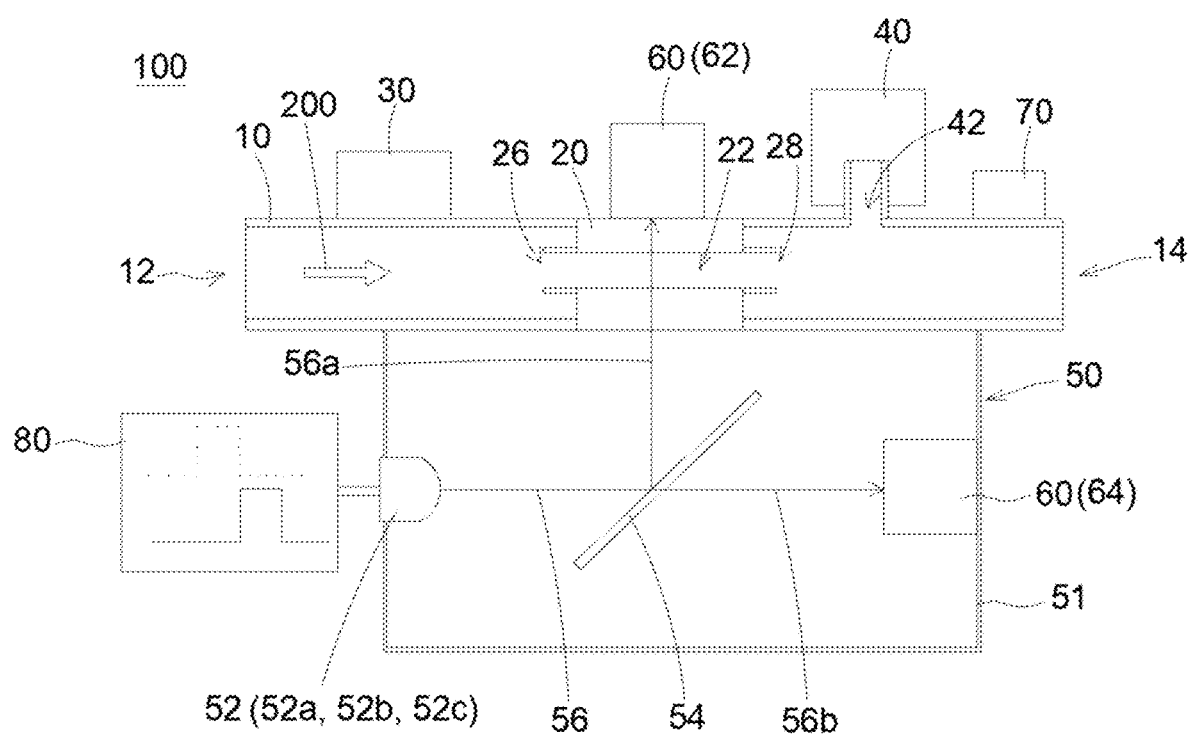
FIG. 3 is a schematic diagram of the device for gas concentration measurement of the disclosure, in which the light-emitting source generates a calibration light beam.
Figure 4:
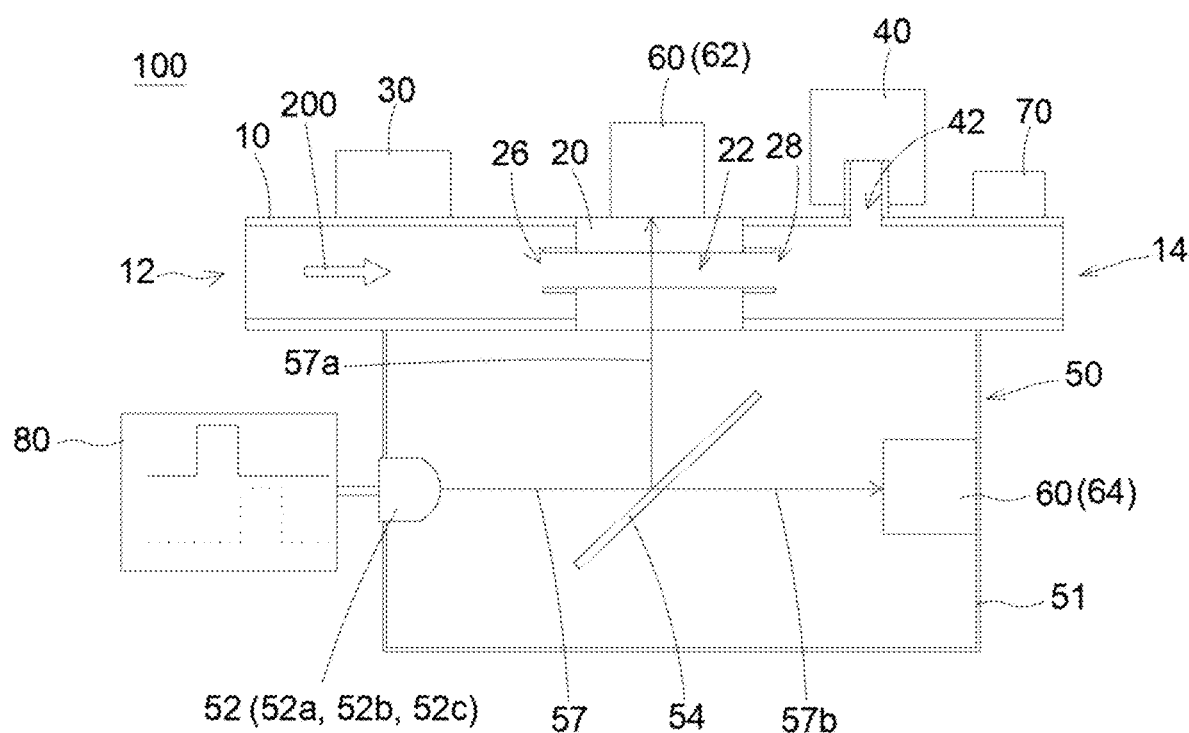
FIG. 4 is a schematic diagram of the device for gas concentration measurement of the disclosure, in which the light-emitting source generates a second detection light beam.
Figure 5:
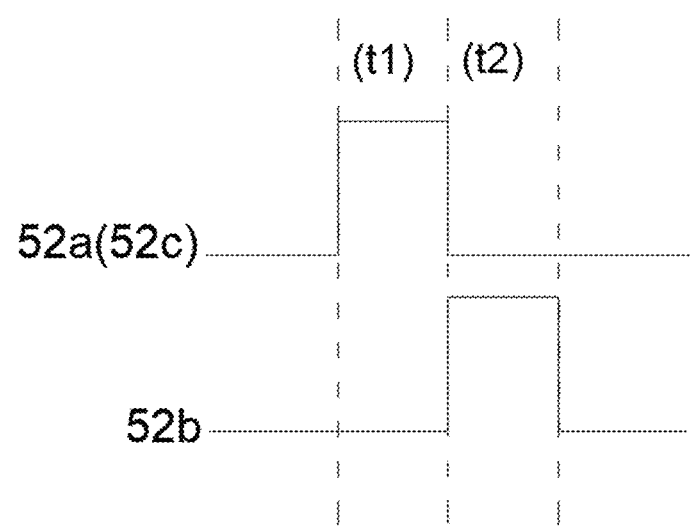
FIG. 5 is a schematic diagram of operation of a light source supply device of the device for gas concentration measurement of the disclosure.

Please refer to FIGS. 1 to 5. FIG. 1 is a flow chart of a method for gas concentration measurement of the disclosure. FIG. 2 is a schematic diagram of a device for gas concentration measurement of the disclosure, in which a light-emitting source generates a first detection light beam. FIG. 3 is a schematic diagram of the device for gas concentration measurement of the disclosure, in which the light-emitting source generates a calibration light beam. FIG. 4 is a schematic diagram of the device for gas concentration measurement of the disclosure, in which the light-emitting source generates a second detection light beam. FIG. 5 is a schematic diagram of operation of a light source supply device of the device for gas concentration measurement of the disclosure.

As shown in FIG. 1, and please refer to FIGS. 2 to 5 at the same time, a method for gas concentration measurement of the disclosure at least comprising following steps of: step S10, providing a gas detection chamber, wherein the gas detection chamber communicates to a gas inlet and outlet channel, so that a cavity of the gas detection chamber contains the to-be-measured gas; step S12, performing a temperature detection step for detecting a gas temperature of the to-be-measured gas; step S14, performing a pressure detection step for detecting a gas pressure of the to-be-measured gas; step S16, providing a first detection light beam and a calibration light beam, wherein an absorbance of the to-be-measured gas for the first detection light beam is greater than an absorbance of the to-be-measured gas for the calibration light beam; step S18, performing a spectroscopic step for splitting the first detection light beam into a first detection split light and a second detection split light respectively passing through and not passing through the gas detection chamber and the to-be-measured gas in the gas detection chamber, and splitting the calibration light beam into a first calibration split light and a second calibration split light respectively passing through and not passing through the gas detection chamber and the to-be-measured gas in the gas detection chamber; step S20, performing a light intensity measurement step for measuring a light intensity of the first detection split light and a light intensity of the second detection split light of the first detection light beam after passing through the to-be-measured gas, wherein a light intensity change in the above light intensity measurement step is caused by the to-be-measured gas and the gas detection chamber, thereby calculating a first detection concentration of the to-be-measured gas; and step S22, performing a calibration step for measuring a light intensity of the first calibration split light and a light intensity of the second calibration split light of the calibration light beam respectively after passing through the to-be-measured gas, wherein a light intensity change in the above calibration step is caused by the gas detection chamber, thereby calculating a calibration concentration (i.e., errors caused by the gas detection chamber) of the to-be-measured gas, wherein the gas concentration of the to-be-measured gas is obtained after subtracting the calibration concentration from the first detection concentration. Although the disclosure illustrates the method for gas concentration measurement with the above sequence of steps, the disclosure is not limited thereto. Any sequence of steps, even adding or deleting steps, as long as the gas concentration of the to-be-measured gas could be obtained, it falls within the scope of protection claimed by the disclosure.

A device for gas concentration measurement 100 of the disclosure at least comprises a gas detection chamber 20, a temperature sensing element 30, a pressure sensing element 40, a light source supply device 50 and a light sensing device 60. The gas detection chamber 20 is communicated to a gas inlet and outlet channel 10, so that a cavity 22 of the gas detection chamber 20 contains a to-be-measured gas 200, thereby measuring a gas concentration of the to-be-measured gas 200. Two ends of the gas inlet and outlet channel 10 are respectively a channel air inlet hole 12 and a channel air outlet hole 14, which are used to correspondingly introduce and export the to-be-measured gas 200. Although the disclosure uses ozone as the to-be-measured gas 200 to illustrate the device and the method for gas concentration measurement of the disclosure, it is not intended to limit the disclosure. Any gas suitable for using in the device and the method for gas concentration measurement of the disclosure falls within the scope of protection claimed by the disclosure.

The channel air inlet hole 12 of the gas inlet and outlet channel 10 is, for example, communicated to a supply source (not shown in the figures) of the to-be-measured gas 200, thereby introducing the to-be-measured gas 200 provided by the supply source into the gas inlet and outlet channel 10. The channel air outlet hole 14 of the gas inlet and outlet channel 10 is, for example, communicated to an application end (not shown in the figures) of the to-be-measured gas 200, such as but not limited to a sterilization equipment or a semiconductor wafer processing chamber. The to-be-measured gas 200, the supply source of the to-be-measured gas 200 and the application end of the to-be-measured gas 200 of the disclosure are not limited to the above examples. Any supply source of the to-be-measured gas 200 and all feasible applications fall within the scope of protection claimed by the disclosure.

The gas detection chamber 20 is communicated to the gas inlet and outlet channel 10, for example, located between two ends of the gas inlet and outlet channel 10. Wherein the gas detection chamber 20 is, for example, a quartz glass tube made of transparent material such as quartz glass, wherein at least upper and lower ends of the quartz glass tube are, for example, a transparent material such as quartz glass. The gas detection chamber 20 is not limited to quartz glass, and could also be made of other materials. As long as it has low or no absorbance for the detection light beam and the calibration light beam, it is applicable in the disclosure. The gas detection chamber 20 is, for example, a hollow chamber 24 having the cavity 22. Two ends of the hollow chamber 24 have a detection gas inlet hole 26 and a detection gas outlet hole 28 respectively communicated to the cavity 22 of the hollow chamber 24. The to-be-measured gas 200, for example, continuously flows through the cavity 22 of the hollow chamber 24 of the gas detection chamber 20.

The temperature sensing element 30 is, for example, disposed on the gas inlet and outlet channel 10 to detect a gas temperature of the to-be-measured gas 200. The pressure sensing element 40 is, for example, disposed on the gas inlet and outlet channel 10, and is communicated to the gas inlet and outlet channel 10 internally via a pressure sensing inlet port 42, for detecting a gas pressure of the to-be-measured gas 200 inside the gas inlet and outlet channel 10. However, type, form and disposed position of the temperature sensing element 30 and the pressure sensing element 40 are not particularly limited. In one embodiment of the disclosure, the temperature sensing element 30 and the pressure sensing element 40 could be any existing commercially available elements and could be, for example, disposed on the gas inlet and outlet channel 10, the gas detection chamber 20 and/or the supply source of the to-be-measured gas 200, as long as it could be used to detect a gas temperature and a gas pressure of the to-be-measured gas 200, it could be applied to the disclosure.

The light source supply device 50 of the device for gas concentration measurement 100 of the disclosure comprises at least one light-emitting source 52 and a light beam splitter 54. The disclosure is capable of splitting a light beam emitted by the light-emitting source 52 of the light source supply device 50 into two sub-light beams through the light beam splitter 54. The two sub-light beams respectively passing through and without passing through the to-be-measured gas 200 in the gas detection chamber 20. Then, the light sensing device 60 is used to measure intensities of the two sub-light beams respectively. If the to-be-measured gas 200 has a higher absorbance for the sub-light beams, an intensity difference between the two sub-light beams comes from the to-be-measured gas 200 and the gas detection chamber 20, which means that an attenuation of light intensity is caused by the to-be-measured gas 200 and the gas detection chamber 20. However, when the to-be-measured gas 200 has a lower absorbance (the lower the absorbance, the better, or having no absorbance is even better) for the sub-light beams, then an intensity difference between the two sub-light beams only comes from the gas detection chamber 20. This means that an attenuation of light intensity is only caused by the gas detection chamber 20, such as light absorbance interference errors caused by dirt or sediment on a tube wall of the gas detection chamber 20. In other words, the disclosure is capable of providing light beams of two different wavelengths through the light-emitting source 52 (i.e., with high absorbance of the to-be-measured gas and low absorbance of the to-be-measured gas or no absorbance of the to-be-measured gas). By eliminating the light absorption interference errors caused by dirt or sediment on a tube wall of the gas detection chamber 20, a gas concentration of the to-be-measured gas 200 could be accurately detected.

In one embodiment of the disclosure, the light source supply device 50 is, for example, disposed on a first side of the gas detection chamber 20 in order to use the light-emitting source 52 on the first side of the gas detection chamber 20 to provide a first detection light beam 55 and a calibration light beam 56 respectively. The light-emitting source 52 is, for example, a light-emitting diode element, thereby improving the problem of low utilization rate caused by traditional ultraviolet light sources diverging around. The light source supply device 50 has, for example, but is not limited to, a cover 51 disposed on the first side of the gas detection chamber 20, and the light-emitting source 52 and the light beam splitter 54 are located inside the cover 51. However, the cover 51 is not limited to having a hollow interior or a solid interior. For example, the disclosure is capable of generating the first detection light beam 55 through a first light-emitting diode element (LED) 52a and generating the calibration light beam 56 through a second light-emitting diode element 52b respectively. However, the disclosure is not limited thereto. The disclosure is also capable of generating the first detection light beam 55 and the calibration light beam 56 respectively through, for example, a single light-emitting diode element (LED). One feature of the disclosure is that an absorbance of the to-be-measured gas 200 for the first detection light beam 55 is preferably greater than an absorbance of the to-be-measured gas 200 for the calibration light beam 56, wherein the larger a difference between the two absorbances, the better. For example, a wavelength of the first detection light beam 55 is within an absorption wavelength range of the to-be-measured gas 200, and a wavelength of the calibration light beam 56 could be within or outside an absorption wavelength range of the to-be-measured gas 200, as long as an absorbance of the to-be-measured gas 200 for the first detection light beam 55 is greater than an absorbance of the to-be-measured gas 200 for the calibration light beam 56, it is applicable in the disclosure. Wherein a wavelength of the calibration light beam 56 is preferably outside an absorption wavelength range of the to-be-measured gas 200, which means that when the calibration light beam 56 passes through the to-be-measured gas 200 in the cavity 22 of the gas detection chamber 20, the calibration light beam 56 will not be absorbed by the to-be-measured gas 200, so an error caused by the gas detection chamber 20 could be obtained. Taking the to-be-measured gas 200 as ozone as an example, the first detection light beam 55 and the calibration light beam 56 are, for example, ultraviolet lights of different wavelengths, ranging from about 200 nm to about 370 nm, or the calibration light beam 56 is outside the above wavelength range. Wherein an ultraviolet absorbance of the first detection light beam 55 is higher than an ultraviolet absorbance of the calibration light beam 56. An absorption spectrum of ozone is between about 200 nm and about 370 nm, and a maximum absorption wavelength is about 254 nm. Therefore, the disclosure could, for example, use the first light-emitting diode element 52a with an ultraviolet light wavelength of 254 nm, which has a maximum absorption of ozone gas, to generate the first detection light beam 55, and use the second light-emitting diode element 52b with an ultraviolet light wavelength of 385 nm, which has a minimum absorption of ozone gas, to generate the first calibration light beam 56. In addition, the disclosure preferably turns on and off the first light-emitting diode element 52a and the second light-emitting diode element 52b alternately (for example, in an alternate manner such as interval type or pulse type). Taking the pulse type as an example, a pulse width could be, for example, any numerical value between 0.1 ms and 5 ms, a period could be, for example, any numerical value between 0.1 s and 1 s, and a frequency could be, for example, any numerical value between 100 Hz and 1 Hz. Taking the interval type as an example, the disclosure could repeatedly turn on and off the first detection light beam 55 and the calibration light beam 56 at regular time intervals, for example. The above data are only examples and are not intended to limit the scope of the disclosure. As shown in FIGS. 2 and 5, an interval (t1) represents that the first light-emitting diode element 52a is in an on state, and the second light-emitting diode element 52b is in an off state. As shown in FIG. 3 and FIG. 5, an interval (12) represents that the first light-emitting diode element 52a is in an off state, and the second light-emitting diode element 52b is in an on state. The above-mentioned intervals are, for example, time intervals. According to the Beer-Lambert law, the disclosure is capable of detecting ozone gas in the Hartley-Huggins spectrum absorption band (200 nm-370 nm). For example, a maximum value of an ozone gas concentration that could be detected by the disclosure is about 400 g/Nm$^3$, wherein g is gram and Nm$^3$ is standard cubic meter. Alternatively, for example, a range of ozone gas concentration that could be detected by the disclosure is between 1 ppm and 250 ppm.

As mentioned above, the light beam splitter 54 of the disclosure is capable of splitting the first detection light beam 55 into a first detection split light 55a and a second detection split light 55b (as shown in FIG. 2), and splitting the calibration light beam 56 into a first calibration split light 56a and a second calibration split light 56b (as shown in FIG. 3). Wherein the first detection split light 55a and the first calibration split light 56a pass through the gas detection chamber 20 and the to-be-measured gas 200, and the second detection split light 55b and the second calibration split light 56b do not pass through the gas detection chamber 20 and the to-be-measured gas 200. The light beam splitter 54 is, for example, a tilted light beam splitting plate, which is disposed between the light-emitting source 52 and a second light sensing element 64 (as described later), thereby causing the first detection split light 55a and the first calibration split light 56a having a same first optical path, the second detection split light 55b and the second calibration split light 56b having a same second optical path.

In addition, the light sensing device 60 of the device for gas concentration measurement 100 of the disclosure at least comprises a first light sensing element 62 and a second light sensing element 64 located on a second side and the first side of the gas detection chamber 20 respectively. After the first detection light beam 55 (ultraviolet light) provided by the light-emitting source 52 of the disclosure passes through the light beam splitter 54, the first detection split light 55a will pass through the gas detection chamber 20 made of quartz glass along the first optical path and then reach the first light sensing element 62 to establish a light intensity containing the to-be-measured gas 200 (ozone gas) and the gas detection chamber 20. After the first detection light beam 55 (ultraviolet light) passes through the light beam splitter 54, the second detection split light 55b reaches the second light sensing element 64 along the second optical path to establish a light intensity without the to-be-measured gas 200 (ozone gas) and without the gas detection chamber 20. In the same way, the disclosure could also respectively establish a light intensity containing the to-be-measured gas 200 (ozone gas) and the gas detection chamber 20 and a light intensity without the to-be-measured gas 200 (ozone gas) and without the gas detection chamber 20 for the first calibration split light 56a and the second calibration split light 56b of the calibration light beam 56 provided by the light-emitting source 52.

According to the Beer-Lambert law well known to those having ordinary skill in the art to which the disclosure pertains, when light penetrates a gas, an absorption rate (or called absorbance) of light is directly proportional to absorption coefficient, optical path length and gas concentration. Therefore, the disclosure could calculate the first detection concentration and the calibration concentration of the to-be-measured gas 200 by, for example, Beer-Lambert law, and obtain a gas concentration of the to-be-measured gas 200 after subtracting the calibration concentration from the first detection concentration.

In short, the first light sensing element 62 and the second light sensing element 64 of the light sensing device 60 of the disclosure could respectively measure a light intensity of the first detection split light 55a and a light intensity of the second detection split light 55b of the first detection light beam 55, thereby calculating the first detection concentration of the to-be-measured gas 200, and respectively measure a light intensity of the first calibration split light 56a and a light intensity of the second calibration split light 56b of the calibration light beam 56, thereby calculating the calibration concentration of the to-be-measured gas 200, wherein a gas concentration of the to-be-measured gas 200 could be obtained after subtracting the calibration concentration from the first detected concentration.

The formula for calculating a concentration of various gases according to Beer-Lambert law:

$$C_{O_3} = -\frac{1}{\alpha \times l} \times \frac{T}{273°K} \times \frac{14.695 psi}{P} \times \ln\frac{I}{I_0}.$$

Taking the to-be-measured gas 200 as ozone as an example, I is a numerical value of UV light intensity (first optical path) containing ozone gas, $I_0$ is a numerical value of UV light intensity (second optical path) without ozone gas, a is an absorption coefficient of ozone gas, P is a gas pressure of ozone gas, T is a gas temperature (in degree K) of ozone gas, psi is a pressure (in pounds per square inch (absolute)), 1 is an optical path length of ozone gas.

In detail, the device for gas concentration measurement 100 of the disclosure, for example, further comprises a processing element 70. The processing element 70 is, for example, electrically connected to the light sensing device 60, the temperature sensing element 30 and the pressure sensing element 40. The processing element 70 is, for example, a processing control element. For example, the processing element 70 places a gas temperature of the to-be-measured gas 200, a gas pressure of the to-be-measured gas 200, a light intensity of the first detection split light 55a, a light intensity of the second detection split light 55b, an optical path length of the to-be-measured gas 200 in the cavity 22 of the gas detection chamber 20, and an absorption coefficient of the to-be-measured gas 200 into the formula for calculating a concentration $C_{O_3}$ of various gases disclosed by the Beer-Lambert law in order to calculate the first detection concentration $C_{O_3}1$ of the to-be-measured gas 200. Wherein the processing element 70, for example, further places a gas temperature of the to-be-measured gas 200, a gas pressure of the to-be-measured gas 200, a light intensity of the first calibration split light 56a, a light intensity of the second calibration split light 56b, an optical path length of the to-be-measured gas 200 in the cavity 22 of the gas detection chamber 20, and an absorption coefficient of the to-be-measured gas 200 into the formula for calculating an ozone concentration $C_{O_3}$ disclosed by the Beer-Lambert law in order to calculate the calibration concentration $C_{O_3}2$ of the to-be-measured gas 200. Wherein a gas concentration $C_{O_3}3$ of the to-be-measured gas 200 could be obtained after subtracting the calibration concentration $C_{O_3}2$ from the first detected concentration $C_{O_3}1$ (i.e., $C_{O_3}1 - C_{O_3}2 = C_{O_3}3$).

The light source supply device 50 of the disclosure further optionally comprises a light source control element 80 for controlling the light-emitting source 52 of the light source supply device 50 to alternately provide the first detection light beam 55 and the calibration light beam 56 in a light-emitting mode. For example, the light source control element 80 is, but not limited to, an ultraviolet light source pulse controller. The processing element 70 is, for example, electrically connected to the light source control element 80. Wherein the light-emitting mode is, for example, pulse type or interval type opening and closing to provide the first detection light beam 55 and the calibration light beam 56. In addition, the light-emitting source 52 has, for example, one light-emitting element or a plurality of light-emitting elements for providing the first detection light beam 55 and the calibration light beam 56. For example, the disclosure could provide the first detection light beam 55 and the calibration light beam 56 by respectively using a plurality of light-emitting elements, such as the first light-emitting diode element 52a and the second light-emitting diode element 52b. The first light-emitting diode element 52a generates, for example, the first detection light beam 55, and the second light-emitting diode element 52b generates, for example, the calibration light beam 56. However, the disclosure is not limited thereto. Since a single light-emitting diode element (LED) may also contain a plurality of solid-state light-emitting diode crystalline grains of different wavelengths, the disclosure, for example, could also generate the first detection light beam 55 and the calibration light beam 56 respectively by using a single light-emitting element (such as a light-emitting diode element). In addition, the disclosure, for example, could also adjust a brightness and/or a wavelength of the first detection light beam 55 and the calibration light beam 56 through the light source control element 80.

In addition, another feature of the disclosure is that when the gas concentration $C_{o_3}$ 3 of the to-be-measured gas 200 obtained after subtracting the calibration concentration $C_{o_3}$ 2 from the first detection concentration $C_{o_3}$ 1 is lower than a preset value, the light-emitting source 52 could provide at least one second detection light beam 57 to replace a role of the first detection light beam 55, as shown in FIG. 4. Wherein the light beam splitter 54 will also split the second detection light beam 57 into a third detection split light 57*a* and a fourth detection split light 57*b*, thereby obtaining the first detection concentration $C_{o_3}$ 1 like the first detection light beam 55. Wherein a wavelength and/or a brightness of the second detection light beam 57 are/is different from a wavelength and/or a brightness of the first detection light beam 55. Wherein the gas concentration $C_{o_3}$ 3 of the to-be-measured gas 200 could be obtained after subtracting the calibration concentration $C_{o_3}$ 2 from the first detection concentration $C_{o_3}$ 1 (i.e., $C_{o_3}$ 1-$C_{o_3}$ 2=$C_{o_3}$ 3). The disclosure is not limited to changing a wavelength or a brightness of the detection light beam in manual mode or automatic mode. Taking the automatic mode to change a wavelength of the detection light beam as an example, when the gas concentration of the to-be-measured gas 200 (for example, ozone) is detected to be lower than a certain preset value, for example, lower than 10% of a preset scale (for example, full scale), the light source control element 80 could, for example, control the light-emitting source 52 to immediately or subsequently change to a third light-emitting diode element 52*c* to provide the second detection light beam 57. Wherein the third light-emitting diode element 52*c* is, for example, a light source that absorbs low-concentration ozone. However, the disclosure is not limited thereto. The disclosure could also generate the second detection light beam 57 to replace the first detection light beam 55 by using a single light-emitting diode element (LED). A light-emitting mode between the second detection light beam 57 and the calibration light beam 56 is, for example, the same as a light-emitting mode between the first detection light beam 55 and the calibration light beam 56.

The disclosure utilizes the characteristics that the same to-be-measured gas (such as ozone) has different absorbances for light of different wavelengths, and utilizes the corresponding relationship between an absorbance of light of the same wavelength and the gas concentration of the to-be-measured gas (such as ozone), the gas concentration of the to-be-measured gas could be accurately detected in real time. Although the disclosure takes the to-be-measured gas as ozone as an example, the disclosure is not limited thereto. For any gas that has different absorbances for different light wavelengths, the device and the method for gas concentration measurement of the disclosure could be used to measure the gas concentration of this gas. The disclosure could not only be used to measure and calibrate the to-be-measured gas in a flowing or non-flowing state, but could even be used to measure the to-be-measured gas in continuous flow and perform calibration in real time. For example, the disclosure could be used to feed back the supply source of the to-be-measured gas (such as ozone generator or sterilization equipment) to produce ozone gas with sufficient concentration. For example, if the supply source of the to-be-measured gas supplies the to-be-measured gas in a continuous flow, the disclosure could further achieve an efficacy of instantaneous, accurate and rapid measurement of the gas concentration of the continuously flowing to-be-measured gas. For example, in response to the to-be-measured gas with different concentration ranges, the detection light beam with a corresponding wavelength could be replaced instantly, and an efficacy of real-time calibration could also be provided. The device and the method for gas concentration measurement of the disclosure could be applied to application ends of the to-be-measured gas such as sterilization equipment, semiconductor wafer manufacturing or ozone generators that require accurate, stable and quick feedback of ozone concentration.

Based on the above, the device and the method for gas concentration measurement of the disclosure have the following efficacies:

(1) Compared with the traditional technology of using a low-pressure mercury lamp as an ultraviolet light-emitting source, the device for gas concentration measurement of the disclosure uses a small light-emitting diode element as an ultraviolet light-emitting source (UV-LED), which could respond to ozone gas in different concentration ranges, so there is no need to replace the machine.

(2) The disclosure uses the light-emitting diode element as the ultraviolet light-emitting source and does not require startup warm-up time. Therefore, the ultraviolet light-emitting source could be provided in a pulse switch manner to achieve instant calibration.

(3) The disclosure uses the light-emitting diode element as the ultraviolet light-emitting source to instantly, accurately and quickly measure a gas concentration of the continuously flowing to-be-measured gas. It does not require preheating, has low starting voltage, does not have mercury vapor, and has a long service life.

(4) The disclosure could instantly change and provide detection light beams of different wavelengths in response to the to-be-measured gas in different concentration ranges, thereby providing real-time calibration and feedback.

(5) The disclosure could solve the problem of measurement errors caused by contaminated quartz glass tube walls in the traditional technology.

Note that the specification relating to the above embodiments should be construed as exemplary rather than as limitative of the present disclosure, with many variations and modifications being readily attainable by a person of average skill in the art without departing from the spirit or scope thereof as defined by the appended claims and their legal equivalents.

What is claimed is:

1. A device for gas concentration measurement for measuring a gas concentration of a to-be-measured gas, at least comprising:
   a gas detection chamber, the gas detection chamber being communicated to a gas inlet and outlet channel, so that a cavity of the gas detection chamber contains the to-be-measured gas;
   a temperature sensing element for detecting a gas temperature of the to-be-measured gas in the cavity of the gas detection chamber;
   a pressure sensing element for detecting a gas pressure of the to-be-measured gas in the cavity of the gas detection chamber;
   a light source supply device provided on a first side of the gas detection chamber, comprising:
      at least one light-emitting source for providing a first detection light beam and a calibration light beam, wherein an absorbance of the to-be-measured gas for the first detection light beam is greater than an absorbance of the to-be-measured gas for the calibration light beam; and
      a light beam splitter for splitting the first detection light beam into a first detection split light and a second detection split light and splitting the calibration light beam into a first calibration split light and a second calibration split light, wherein the first detection split light and the first calibration split light pass through the gas detection chamber and the to-be-measured gas in the gas detection chamber, and the second detection split light and the second calibration split light do not pass through the gas detection chamber and the to-be-measured gas in the gas detection chamber; and a light sensing device, the light sensing device at least comprising a first light sensing element and a second light sensing element respectively located on a second side and the first side of the gas detection chamber for respectively measuring a light intensity of the first detection split light and a light intensity of the second detection split light of the first detection light beam, thereby calculating a first detection concentration of the to-be-measured gas, and measuring a light intensity of the first calibration split light and a light intensity of the second calibration split light of the calibration light beam respectively, thereby calculating a calibration concentration of the to-be-measured gas, wherein the gas concentration of the to-be-measured gas is obtained after subtracting the calibration concentration from the first detection concentration, wherein when the gas concentration of the to-be-measured gas obtained after subtracting the calibration concentration from the first detection concentration is lower than a preset value, the light-emitting source provides at least one second detection light beam to replace the first detection light beam, and a wavelength and/or a brightness of the second detection light beam are/is different from a wavelength and/or a brightness of the first detection light beam.

2. The device for gas concentration measurement as claimed in claim 1, wherein two ends of the gas inlet and outlet channel are respectively a channel air inlet hole and a channel air outlet hole for correspondingly introducing and exporting the to-be-measured gas, and the gas detection chamber is a hollow chamber having the cavity, two ends of the hollow chamber having a detection gas inlet hole and a detection gas outlet hole respectively communicated to the cavity of the hollow chamber, wherein the to-be-measured gas continuously flows through the cavity of the hollow chamber of the gas detection chamber.

3. The device for gas concentration measurement as claimed in claim 1, further comprising a processing element calculating the first detection concentration of the to-be-measured gas based on the gas temperature of the to-be-measured gas, the gas pressure of the to-be-measured gas, the light intensity of the first detection split light, the light intensity of the second detection split light, an optical path length of the to-be-measured gas in the cavity of the gas detection chamber, and an absorption coefficient of the to-be-measured gas, wherein the processing element further calculates the calibration concentration of the to-be-measured gas based on the gas temperature of the to-be-measured gas, the gas pressure of the to-be-measured gas, the light intensity of the first calibration split light, the light intensity of the second calibration split light, the optical path length of the to-be-measured gas in the cavity of the gas detection chamber, and the absorption coefficient of the to-be-measured gas.

4. The device for gas concentration measurement as claimed in claim 1, wherein the to-be-measured gas is ozone, and the first detection light beam and the calibration light beam provided by the light-emitting source are ultraviolet light.

5. The device for gas concentration measurement as claimed in claim 1, wherein the light beam splitter is a tilted light beam splitting plate to cause the first detection split light and the first calibration split light having a same first optical path, the second detection split light and the second calibration split light having a same second optical path.

6. The device for gas concentration measurement as claimed in claim 1, wherein the gas detection chamber is a quartz glass tube.

7. The device for gas concentration measurement as claimed in claim 1, wherein the wavelength of the first detection light beam is within an absorption wavelength range of the to-be-measured gas, and a wavelength of the calibration light beam is outside the absorption wavelength range of the to-be-measured gas, thereby calibrating a light absorbance interference error generated by the gas detection chamber.

8. The device for gas concentration measurement as claimed in claim 1, wherein the light source supply device further comprises a light source control element for controlling the light-emitting source of the light source supply device to alternately provide the first detection light beam and the calibration light beam in a light-emitting mode.

9. The device for gas concentration measurement as claimed in claim 8, wherein the light-emitting mode is pulse type or interval type opening and closing to provide the first detection light beam and the calibration light beam.

10. The device for gas concentration measurement as claimed in claim 1, wherein when the gas concentration of the to-be-measured gas obtained after subtracting the calibration concentration from the first detection concentration is lower than 10% of a preset scale, the light-emitting source provides the at least one second detection light beam to replace the first detection light beam, and the wavelength and/or the brightness of the second detection light beam are/is different from the wavelength and/or the brightness of the first detection light beam.

11. The device for gas concentration measurement as claimed in claim 1, wherein the light-emitting source has one light-emitting element or a plurality of light-emitting elements for providing the first detection light beam and the calibration light beam.

12. A method for gas concentration measurement for measuring a gas concentration of a to-be-measured gas, at least comprising following steps of:

providing a gas detection chamber, the gas detection chamber communicating to a gas inlet and outlet channel, so that a cavity of the gas detection chamber contains the to-be-measured gas;

performing a temperature detection step for detecting a gas temperature of the to-be-measured gas;

performing a pressure detection step for detecting a gas pressure of the to-be-measured gas;

providing a first detection light beam and a calibration light beam, wherein an absorbance of the to-be-measured gas for the first detection light beam is greater than an absorbance of the to-be-measured gas for the calibration light beam;

performing a spectroscopic step for splitting the first detection light beam into a first detection split light and a second detection split light respectively passing through and not passing through the gas detection chamber and the to-be-measured gas in the gas detection chamber, and splitting the calibration light beam into a first calibration split light and a second calibration split light respectively passing through and not passing through the gas detection chamber and the to-be-measured gas in the gas detection chamber;

performing a light intensity measurement step for measuring a light intensity of the first detection split light and a light intensity of the second detection split light of the first detection light beam, thereby calculating a first detection concentration of the to-be-measured gas; and performing a calibration step for measuring a light intensity of the first calibration split light and a light intensity of the second calibration split light of the calibration light beam respectively, thereby calculating a calibration concentration of the to-be-measured gas, wherein the gas concentration of the to-be-measured gas is obtained after subtracting the calibration concentration from the first detection concentration, wherein when the gas concentration of the to-be-measured gas obtained after subtracting the calibration concentration from the first detection concentration is lower than a preset value, providing at least one second detection light beam to replace the first detection light beam, and a wavelength and/or a brightness of the second detection light beam are/is different from a wavelength and/or a brightness of the first detection light beam.

13. The method for gas concentration measurement as claimed in claim 12, wherein the to-be-measured gas continuously flows through the cavity of the gas detection chamber.

14. The method for gas concentration measurement as claimed in claim 12, wherein the light intensity measurement step further comprises calculating the first detection concentration of the to-be-measured gas based on the gas temperature of the to-be-measured gas, the gas pressure of the to-be-measured gas, the light intensity of the first detection split light, the light intensity of the second detection split light, an optical path length of the to-be-measured gas in the cavity of the gas detection chamber, and an absorption coefficient of the to-be-measured gas, and the calibration step further comprises calculating the calibration concentration of the to-be-measured gas based on the gas temperature of the to-be-measured gas, the gas pressure of the to-be-measured gas, the light intensity of the first calibration split light, the light intensity of the second calibration split light, the optical path length of the to-be-measured gas in the cavity of the gas detection chamber, and the absorption coefficient of the to-be-measured gas.

15. The method for gas concentration measurement as claimed in claim 12, wherein the to-be-measured gas is ozone, and the first detection light beam and the calibration light beam are ultraviolet light.

16. The method for gas concentration measurement as claimed in claim 12, wherein the spectroscopic step uses a light beam splitter to cause the first detection split light and the first calibration split light having a same first optical path, the second detection split light and the second calibration split light having a same second optical path.

17. The method for gas concentration measurement as claimed in claim 12, wherein the gas detection chamber is a quartz glass tube.

18. The method for gas concentration measurement as claimed in claim 12, wherein the wavelength of the first detection light beam is within an absorption wavelength range of the to-be-measured gas, and a wavelength of the calibration light beam is outside the absorption wavelength range of the to-be-measured gas, thereby calibrating a light absorbance interference error generated by a material of the gas detection chamber.

19. The method for gas concentration measurement as claimed in claim 12, further comprising using a light source control element for controlling a light-emitting source to alternately provide the first detection light beam and the calibration light beam in a light-emitting mode.

20. The method for gas concentration measurement as claimed in claim 19, wherein the light-emitting mode is pulse type or interval type opening and closing to provide the first detection light beam and the calibration light beam.

21. The method for gas concentration measurement as claimed in claim 12, wherein when the gas concentration of the to-be-measured gas obtained after subtracting the calibration concentration from the first detection concentration is lower than 10% of a preset scale, providing the at least one second detection light beam to replace the first detection light beam, and the wavelength and/or the brightness of the second detection light beam are/is different from the wavelength and/or the brightness of the first detection light beam.

22. The method for gas concentration measurement as claimed in claim 12, further comprising using a light-emitting source having one light-emitting element or a plurality of light-emitting elements for providing the first detection light beam and the calibration light beam.

* * * * *